US006857915B2

(12) United States Patent
Ciurzynski et al.

(10) Patent No.: US 6,857,915 B2
(45) Date of Patent: Feb. 22, 2005

(54) WIRE BONDING SURFACE FOR CONNECTING AN ELECTRICAL ENERGY STORAGE DEVICE TO AN IMPLANTABLE MEDICAL DEVICE

(75) Inventors: David R. Ciurzynski, Attica, NY (US); Kenneth L. Grubb, Snyder, NY (US)

(73) Assignee: Wilson Greatbatch Technologies, Inc., Clarence, NY (US)

(*) Notice: Subject to any disclaimer, the term of this patent is extended or adjusted under 35 U.S.C. 154(b) by 0 days.

(21) Appl. No.: 10/663,937

(22) Filed: Sep. 16, 2003

(65) Prior Publication Data

US 2004/0040735 A1 Mar. 4, 2004

Related U.S. Application Data

(62) Division of application No. 09/939,351, filed on Aug. 24, 2001, now Pat. No. 6,626,680.

(51) Int. Cl.[7] .............................................. H01R 4/02
(52) U.S. Cl. ........................................ 439/874; 29/874
(58) Field of Search ................................ 439/874–875, 439/877, 883, 889, 909; 29/860, 874, 857; 428/602

(56) References Cited

U.S. PATENT DOCUMENTS

| 542,953 | A | 7/1895 | Von Alimonda et al. |
| 2,246,931 | A | 6/1941 | Chiffey |
| 2,434,992 | A | 1/1948 | Durst |
| 2,568,242 | A | 9/1951 | Matteson, Jr. |
| 2,575,965 | A | 11/1951 | Rock |
| 2,700,087 | A | 1/1955 | Stevens |
| 2,715,169 | A | 8/1955 | HIgh |
| 3,418,422 | A | 12/1968 | Bradham, III |
| 3,519,977 | A | 7/1970 | Swearingen |
| 3,826,000 | A | 7/1974 | Du Rocher et al. |
| 4,151,544 | A | 4/1979 | Riff |
| 4,168,876 | A | 9/1979 | Balde |
| 4,196,960 | A | 4/1980 | Gelfand |
| 4,371,231 | A | 2/1983 | Jung |
| 4,685,467 | A | * 8/1987 | Cartmell et al. ............ 600/385 |
| 4,757,817 | A | * 7/1988 | Healy ......................... 600/392 |
| 5,072,730 | A | 12/1991 | Lee |
| 5,116,700 | A | 5/1992 | Takeda |
| 5,522,861 | A | 6/1996 | Sikorski et al. |
| 5,693,170 | A | 12/1997 | Li |
| 5,877,472 | A | 3/1999 | Campbell et al. |

\* cited by examiner

*Primary Examiner*—J. F. Duverne
(74) *Attorney, Agent, or Firm*—Michael F. Scalise

(57) ABSTRACT

A bonding pad for connecting an electrical energy storage device to an implantable medical device, is described. The bonding pad comprises at least two contact surface, one have a channel for receiving the terminal lead of the electrical storage device, the other being relatively planar for contact to the medical device. That way, the channel provide for increased surface area contact with the terminal lead for a more robust connection while the opposite, planar contact surface provides flexibility for contact to a lead of the medical device.

13 Claims, 5 Drawing Sheets

WIRE BONDING SURFACE FOR CONNECTING AN ELECTRICAL ENERGY STORAGE DEVICE TO AN IMPLANTABLE MEDICAL DEVICE

CROSS-REFERENCE TO RELATED APPLICATION

This application is a divisional of application Ser. No. 09/939,351 filed Aug. 24, 2001, now U.S. Pat. No. 6,626,680 to Ciurzynski et al.

BACKGROUND OF THE INVENTION

1. Field of Invention

The present invention relates to a bonding pad having a large area contact surface providing for connection of an electrical energy storage device to an implantable medical device.

2. Prior Art

Implantable medical devices, such as pacemakers, require an electrical energy storage device as a power source that is easily connected to the device. Typically, the terminal leads of the power source are connected to the medical device directly by welding or soldering. The desire to wire bond directly from a medical device to a power source requires special processing of the terminal leads to prepare them for wire bonding. For example, the terminal leads must be flattened and plated with an applicable bonding media, i.e. gold. The flattening and plating process requires multiple operations that deviate from the normal process flow. Also, flattening a terminal lead does not necessarily assure that there is sufficient surface area to effect a robust connection. A cost-effective alternative is a bonding pad.

U.S. Pat. No. 4,371,231 to Jung, for example, is directed to an electrically conductive connection consisting of a very thin gold wire and a metal contact dot situated on an electrical component or on an integrated circuit. The contact dot includes a plurality of rectangular perforation holes contacted by the nailhead of the gold wire. The other end of the gold wire connects to an external terminal. The problem is that it is often unsuitable to directly bond the end of a wire to a contact surface because there is not enough bonding surface.

U.S. Pat. No. 3,418,422 to Bradham III describes an attachment for integrated circuit leads comprising a KOVAR lead electrolessly plated with nickel. Gold is then electrolessly plated over the nickel. The electroless gold and the electroless nickel form a solid solution type of alloy that normally has a minimum melting point of 950° C. The problem is that these multiple plating steps add considerable cost in terms of time and materials to the manufacturing process.

U.S. Pat. No. 5,116,700 to Takeda is similar to Bradham III, but is not intended for wire bonding or brazing. Instead it is directed to a soldering connection which is basically a flat lead used to connect a battery.

SUMMARY OF THE INVENTION

The present invention is directed to a bonding pad comprising at least two contact surfaces. A terminal lead from an electrical energy storage device as a power source is contacted to the pad on a first contact surface and an implantable medical device is contacted to the other contact surface. The bonding pad is made of a material that is easily and reliably connected to the terminal lead and to the medical device. The present invention is further directed to a bonding pad having a channel, groove, recess, or hole to improve the contact surface area between the pad and the terminal lead of the power source. This structure provides a strong, robust joint between the bonding pad and the terminal lead.

The present invention is further directed to the assembly of an electrical energy storage device powering an implantable medical device. The two are electrically connected together by a terminal lead from the electrical energy storage device contacted to one surface of the bonding pad while the implantable medical device is contacted to a second surface of the bonding pad.

These and other features of the present invention will be increasingly more apparent upon consideration of the following detailed description thereof, presented in connection with the following drawings in which like reference numerals identify the elements throughout.

DETAILED DESCRIPTION OF THE PREFERRED EMBODIMENTS

The present invention is directed to a bonding pad having at least two contact surfaces. A first contact surface provides for contact to an electrical energy storage device, preferably through a terminal lead thereof. A second contact surface provides for connection of the bonding pad to an implantable medical device, for example.

The bonding pad may be of any suitable shape and size and may be of any suitable material such as, but not limited to, nickel, a nickel alloy such as KOVAR (29% Ni, 17% Co and 53% Fe), a copper alloy, or a stainless steel alloy such as 446, 29-4-2 or 52 alloy. In addition, the bonding pad is partially or completely plated with, for example but not limited to, gold. The gold, or other appropriate material, provides a transition surface between the bonding pad and the implantable medical device. For example, some manufacturers use gold wires to connect to the implantable medical device. If other materials are used for the leads from the medical device, then the bonding pad is plated accordingly.

The terminal lead from the electrical energy storage device is attached to the first contact surface of the bonding pad, preferably in a channel, recess, groove, or hole designed to accept and receive the terminal lead. The channel, recess, groove, or hole is formed into the bonding pad to allow a better fit and a strong, robust connection between the terminal lead of the electrical energy storage device and the bonding pad. Intimate contact between the bonding pad and terminal lead improves the quality and weldability of the connection. The terminal lead of the electrical energy storage device is joined to the bonding pad in any suitable manner, such as but not limited to, welding, brazing, or soldering. The bonding pad is secured to the terminal of the electrical energy storage device where it is most easily accessible for the joining process with the medical device. In that respect, it may be located anywhere on the electrical energy storage device that does not interfere with the form, fit or function of the storage device.

The second contact surface of the bonding pad is preferably planar. It is also preferred that at least this surface is plated, such as with gold, to improve the connection to the medical device.

Figure 1:
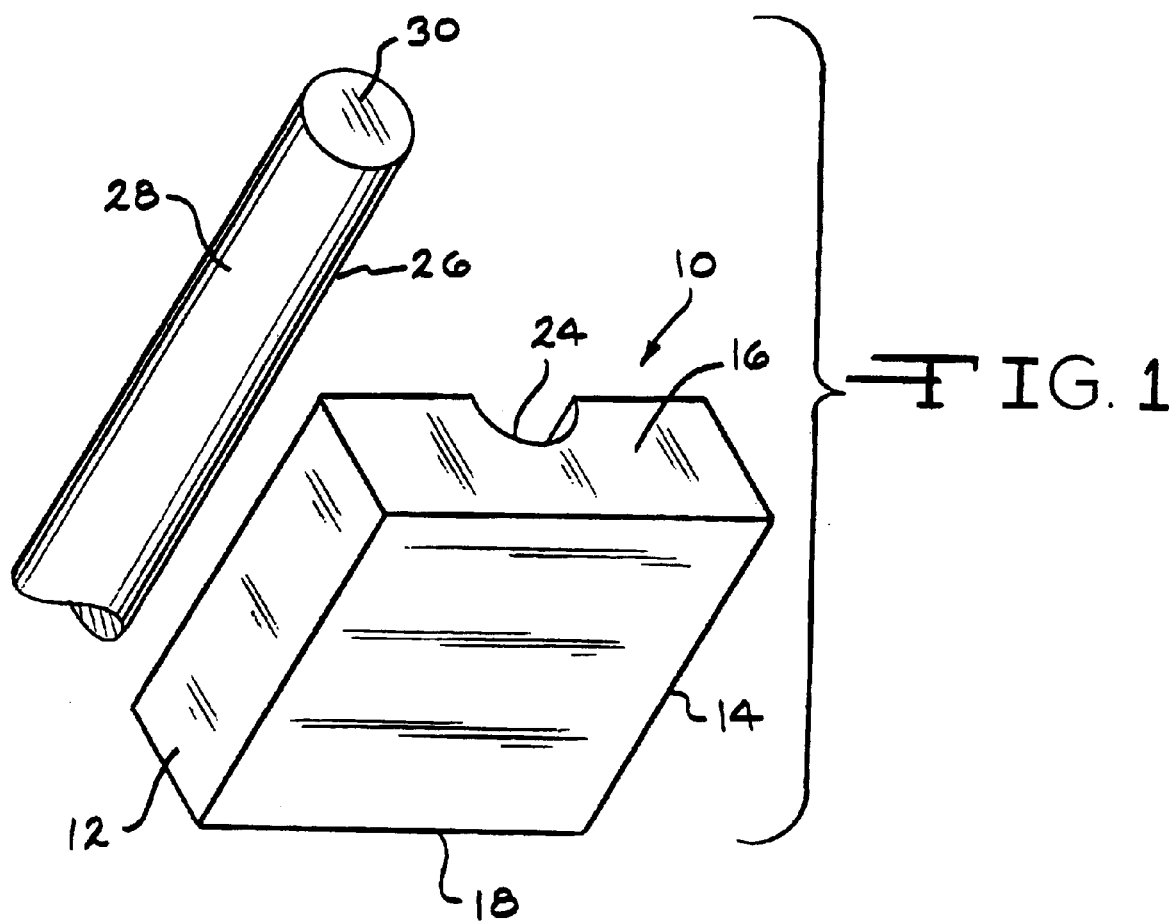
FIG. 1 is a perspective view of a terminal lead 26 being moved toward a bonding pad 10 having a contact surface provided with a channel 24 according to the present invention.
Figure 2:
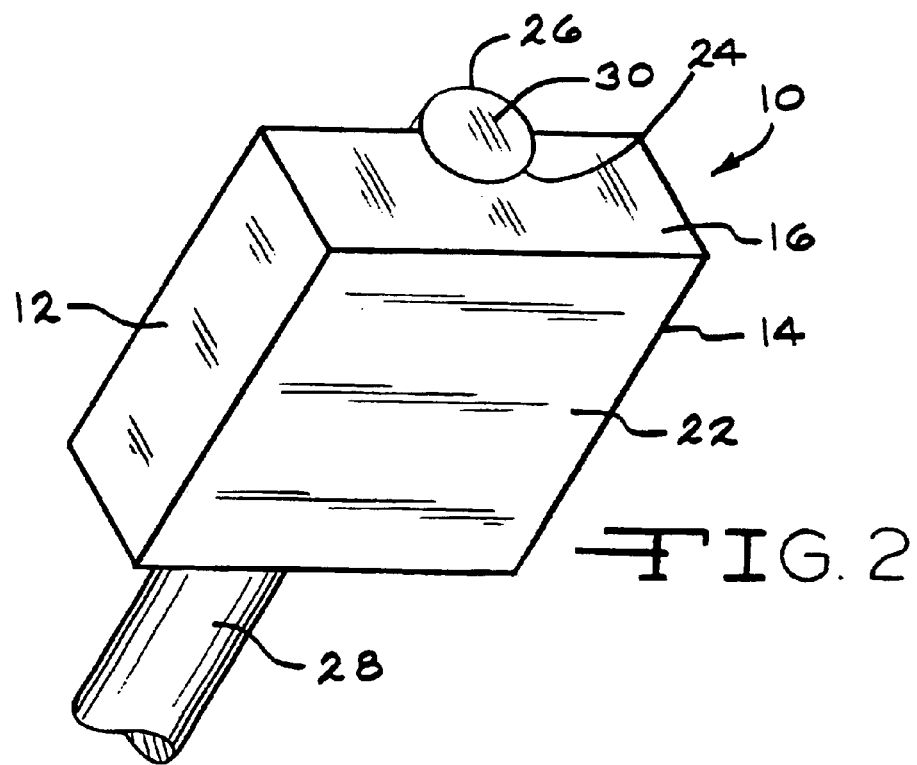
FIG. 2 is a perspective view of the terminal lead 26 shown in FIG. 1 received in the channel 24 of the bonding pad 10.

Turning now to the drawings, FIGS. 1 and 2 show perspective views of a preferred embodiment of the bonding pad 10. The bonding pad 10 comprises spaced apart left and right side walls 12 and 14 extending to and meeting with front and back walls 16 and 18. The side walls 12, 14 and the front and back walls 16, 18 extend to and meet with generally planar upper and lower contact walls 20 and 22. The upper and lower contact walls 20 and 22 provide the bonding pad 10 with a thickness between them.

The upper contact wall 20 is provided with a channel 24 recessed part way into the thickness of the bonding pad 10. The channel 24 has an arcuate shape as viewed from either the front wall 16 or the back wall 18. In that respect, the channel extends from the front wall 16 to the back wall 18 and is spaced about equidistant between the left and right side walls 12, 14.

Figure 6:
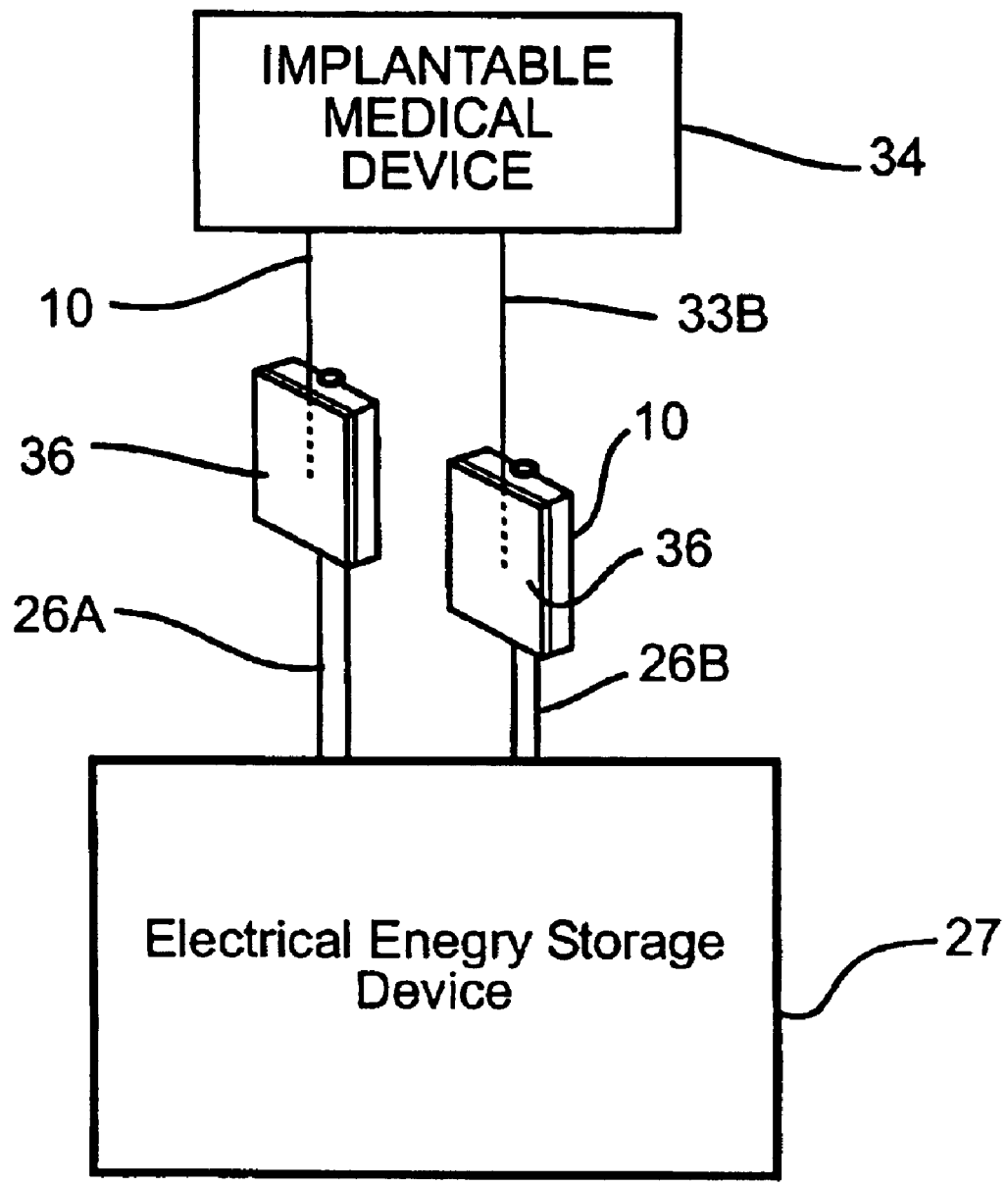
FIG. 6 is a schematic showing an electrical energy storage device 27 electrically connected to an implantable medical device 34 using bonding pads 10 of the present invention for the terminals of both devices.
Figure 7:
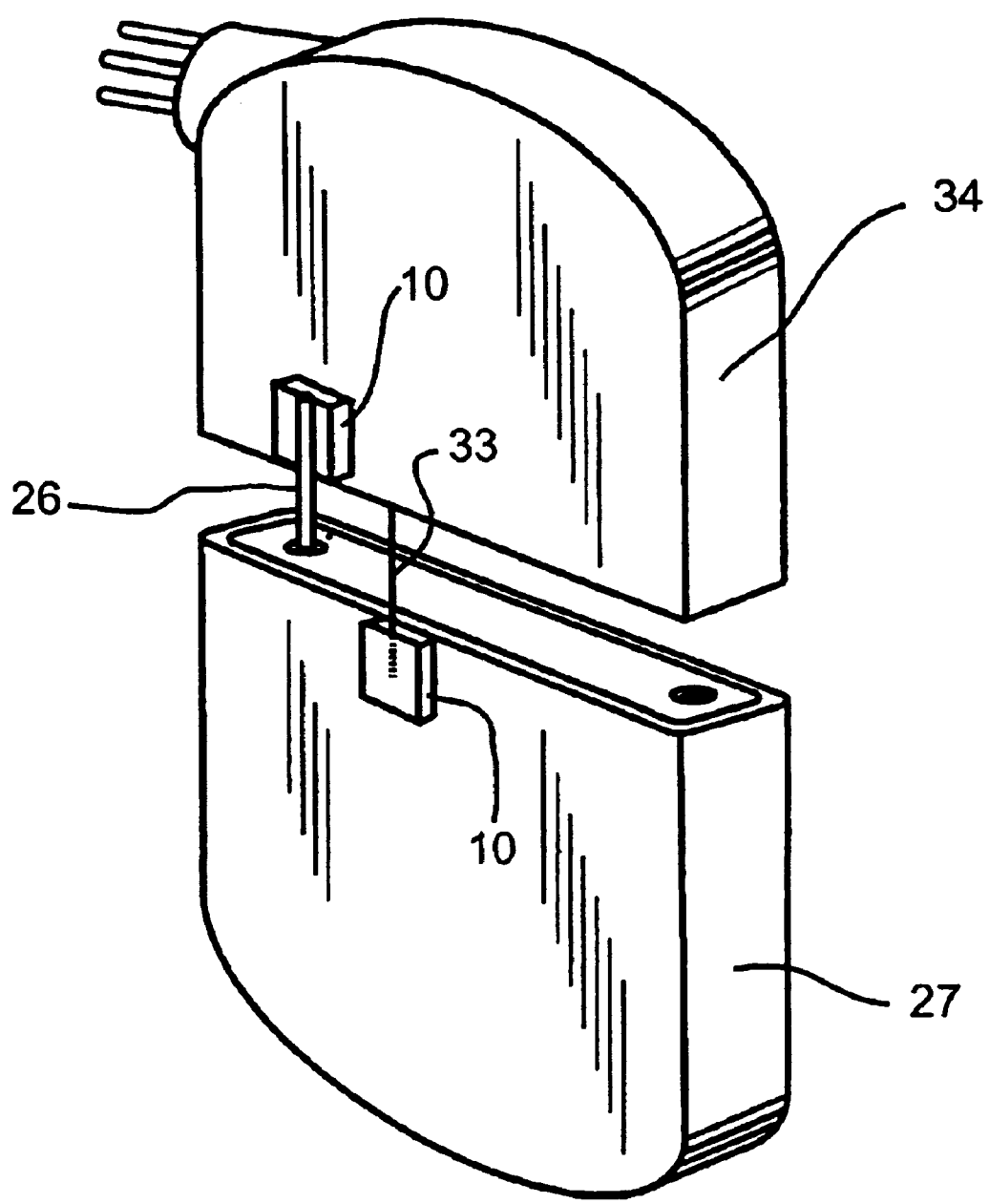
FIG. 7 is a perspective view of a battery 27 showing a bonding pad 10 connecting to a terminal lead 26 there from directly to the housing for the implantable medical device 34 and a second bonding pad 10 connecting a lead 33 from the medical device directly to the enclosure housing the battery.

A terminal lead 26 connected to an electrical energy storage device (FIG. 6), for example, the battery 27 illustrated in FIG. 7, includes a side wall 28 (FIGS. 1 and 2) having a generally circular cross-section along its length. Suitable materials for the terminal lead include molybdenum, titanium, tantalum, and stainless steel alloys such as 446, 29-4-2 and 52 alloys. The circular shape of the terminal lead 26 is preferably sized to match the arcuate shape of the channel 24. That way, when the terminal lead 26 is received and nested in the channel 24 there is a maximum amount of surface area contact between the two.

While an end 30 of the terminal lead 26 is shown in FIG. 2 being generally flush with the front wall 16, that is not necessary. However, it is desirable to have the terminal lead extend beyond the back wall 18 so that the lead is free of the electrical energy storage device 27. In the alternative, it is contemplated that the terminal lead can be bent at a position spaced from its end 30. That is, a portion of the terminal lead is nested or received in the channel, and then spaced from the nested end, the lead is bent so that the remainder of the lead is disposed at an angle with respect to the planar surface of the upper contact surface 20.

Figure 3:
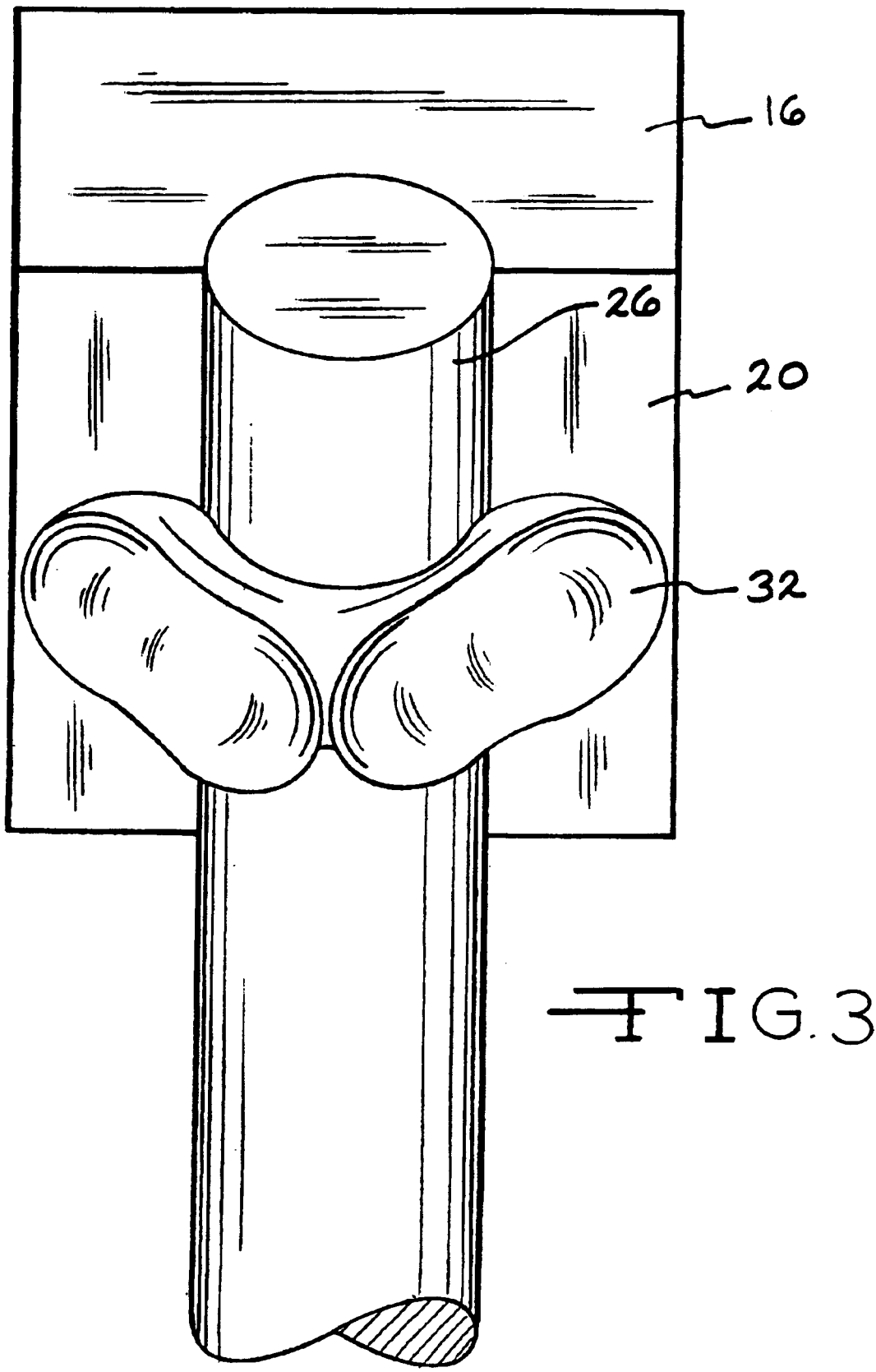
FIG. 3 is a plan view showing the terminal lead 26 of FIG. 2 secured to the bonding pad 10 by a weld 32.
Figure 4:
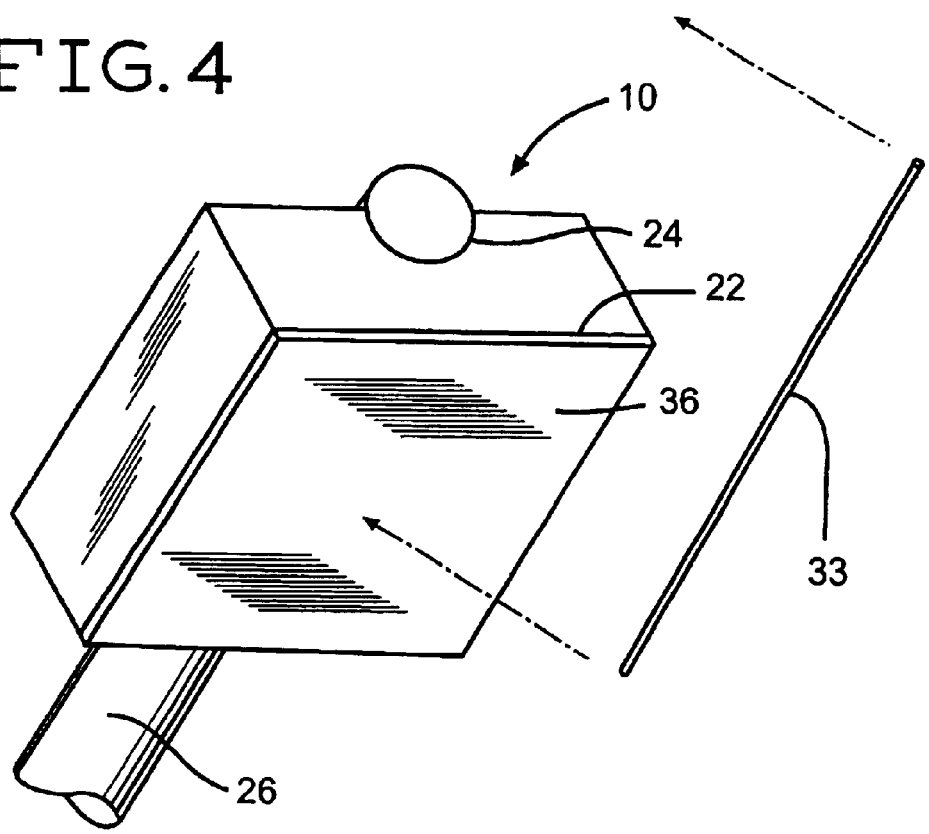
FIG. 4 is a perspective view of the bonding pad 10 prior to contact with a wire 33 from an implantable medical device.
Figure 5:
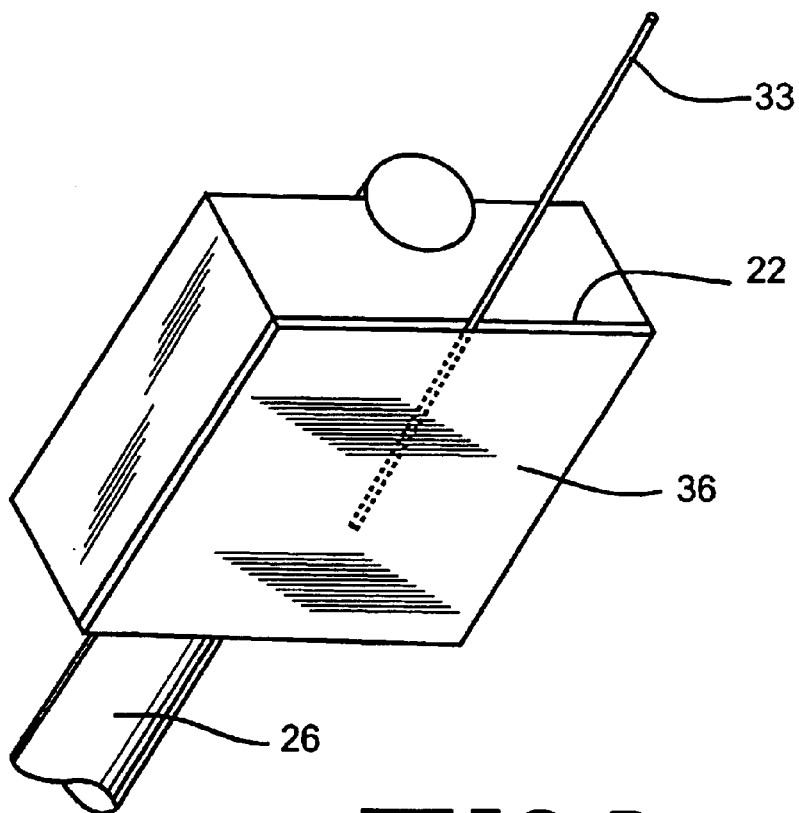
FIG. 5 is a perspective view showing the bonding pad 10 of FIG. 4 with the wire 33 from the medical device contacted to a plated surface 36 of the bonding pad.

As shown in FIG. 3, the terminal lead 26 and the channel 24 are joined to each other by, for example, a weld 32. However, as previously discussed, other connection methods are also contemplated by the scope of the present invention. These alternate methods include brazing, soldering and even adhesives. In that respect, the channel 24 provides an increased surface area for contact with the side wall 28 of the terminal lead 26 while the upper contact wall 20 provides ample surface area for supporting the bonding material, such as the weld 32, securing the terminal lead 26 to the bonding pad 10.

As shown in FIGS. 1, 2, 4 and 5, the lower contact wall 22 of the bonding pad 10 is of a similar planar shape as that of the upper contact wall 20 (FIG. 3). This provides a relatively large contact area for connection of the bonding pad 10 to the implantable medical device (FIG. 6), for example, a lead 33 connecting from the bonding pad to a pacemaker 34, as illustrated in FIG. 7. Preferably, the lower contact wall 22 is provided with a layer 36 of gold plated thereon.

By using the bonding pad 10 of the present invention, normal production processing can be used to manufacture the connection. The prior art approach to obtain a similarly large surface as that provided by the present bonding pad requires non-typical processing steps. For example, additional steps are needed to flatten, gold plate, and modify the terminals of the electrical energy storage device for subsequent connection to the medical device. These non-typical operations add cost to the assembly. The present invention eliminates such additional processing steps required to produce wire bondable terminations.

As shown in FIGS. 1 to 3, the bonding pad 10 is preferably a cube or other six-sided-structure. However, in a broader sense, the bonding pad may be of any suitable shape. The size and shape of the bonding pad can be altered to allow attachment to terminals of various diameters, materials, shapes of electrical energy storage devices, and/or lid surfaces.

Also, the shape of the receiving channel 24 need not be arcuate. Instead, the channel can have a myriad of cross-sectional shapes, limited only by the many shapes in which the side wall of the terminal lead can be practically manufactured. What is important is that the cross-sectional shape of the terminal lead closely matches that of the channel. That way, there is maximum amount of surface area contact between the two for a robust connection. Any suitable welding, brazing, soldering, or adhesive process may be used to connect the opposite polarity terminal leads 26A, 26B (FIG. 6) of the electrical energy storage device to the upper contact wall 20 of the bonding pad 10, and to connect the lower contact wall 22 to the opposite polarity leads 33A, 33B (FIG. 6) from the implantable medical device. It is also contemplated by the scope of the present invention that there may be assemblies where it is more beneficial to connect a side of the bonding pad 10 other than the lower contact surface 22 to a lead from the medical device. In those situations, any one of the left and right side walls 12, 14 and the front wall 16 may be used. If the terminal lead is bent away from the bonding pad, as previously described, the back wall 18 can also be used.

While the bonding pad 10 is preferably used to connect the electrical energy storage device to an implantable medical device, the present invention is not to be limited to use on the terminal pins thereof. As shown in FIG. 7, the present bonding pad can be directly connected to the enclosure housing the electrical energy storage device or the enclosure housing the medical device.

While these particular embodiments of the present invention and advantages have been shown and described in detail, it is recognized that various modifications thereof will occur to those skilled in the art. Therefore, the scope of the herein-described invention shall be limited solely by the claims appended hereto.

What is claimed is:

1. A method for connecting an electrical energy storage device to an implantable medical device, comprising the steps of:
   a) providing a bonding pad comprising:
      i) an intermediate surrounding side wall extending to end meeting with at least two spaced apart first and second contact walls; and
      ii) a recess provided in at least one of the first and second contact walls of the bonding pad, the recess extending to and meeting with spaced apart portions of the surrounding side wall;

b) moving a terminal lead of the electrical energy storage device into a nested position in the recess, the terminal lead comprising a terminal side wall extending along a longitudinal axis thereof, wherein a first portion of the terminal lead side wall extending along the longitudinal axis is received in the recess of the bonding pad to meet at least one of the spaced apart portions of the surrounding side wall and wherein a second portion of the terminal lead side wall extending along the longitudinal axis and opposite at least that part of the first portion meeting with the one of the spaced apart portions of the surrounding side wall is exposed and not in contact with the bonding pad;

c) securing the terminal lead to the bonding pad at least at a region where the one of the first and second contact walls having the recess meets the second portion of the terminal lead; and d) securing the other of the first and second contact walls not having the recess to the implantable medical device.

2. The method of claim 1 including providing the bonding pad comprising spaced apart third and fourth side walls extending to and meeting with spaced apart front and back walls, and wherein the spaced apart first and second contact walls are joined to the third and fourth side walls and the front and back walls.

3. The method of claim 2 including providing the recess as a channel extending to and meeting with at least two of the third and fourth side walls and the front and back walls.

4. The method of claim 1 including securing the terminal lead to the recess by one of welding, brazing, soldering, and an adhesive.

5. The method of claim 1 including securing the other of the first and second contact walls not having the recess to the implantable medical device by one of welding, brazing, soldering, and an adhesive.

6. The method of claim 1 including providing the spaced apart first and second contact walls being generally planar.

7. The method of claim 6 including providing the planar first and second contact walls being parallel to each other.

8. The method of claim 1 including providing the bonding pad of a material selected from the group consisting of nickel, a nickel alloy, a copper alloy, and a stainless steel alloy.

9. The method of claim 1 including partially or completely plating the bonding pad.

10. The method of claim 1 including at least partially plating the bonding pad with gold.

11. The method of claim 1 including providing the terminal lead of a material selected from the group consisting of molybdenum, titanium, tantalum, 446 stainless steel, 29-4-2 stainless steel, 52 alloy, and mixtures thereof.

12. A method for connecting an electrical energy storage device to an implantable medical device, comprising the steps of:

a) providing a bonding pad comprising:
  i) an intermediate surrounding side wall extending to and meeting with at least two spaced apart first and second contact walls; and
  ii) a recess provided in at least one of the first and second contact walls of the bonding pad, the recess extending to and meeting with spaced apart portions of the surrounding side wall; and b) moving a terminal lead of the electrical energy storage device into a nested position in the recess, the terminal lead comprising a terminal side wall extending along a longitudinal axis thereof, wherein a first portion of the terminal lead side wall extending along the longitudinal axis is received in the recess of the bonding pad to meet at least one of the spaced apart portions of the surrounding side wall and wherein a second portion of the terminal lead side wall extending along the longitudinal axis and opposite at least that part of the first portion meeting with the one of the spaced apart portions of the surrounding side wall is exposed and not in contact with the bonding pad;

c) securing the terminal lead to the bonding pad at least at a region where the one of the first and second contact walls having the recess meets the second portion of the terminal lead;

d) securing the other of the first and second contact walls not having the recess to the implantable medical device; and e) providing a second bonding pad comprising a second intermediate surrounding side wall extending to and meeting with at least two spaced apart third and fourth contact walls, wherein one of the third and fourth contact walls is directly connected to an enclosure for the electrical energy storage device and the other of the third and fourth contact walls is electrically connected to the implantable medical device.

13. A method for connecting an electrical energy storage device to an implantable medical device, comprising the steps of:

a) providing a bonding pad comprising:
  i) an intermediate surrounding side wall extending to and meeting with at least two spaced apart first and second contact walls; and
  ii) a recess provided in at least one of the first and second contact walls of the bonding pad, the recess extending to and meeting with spaced apart portions of the surrounding side wall; and b) moving a terminal lead of the electrical energy storage device into a nested position in the recess, the terminal lead comprising a terminal side wall extending along a longitudinal axis thereof, wherein a first portion of the terminal lead side wall extending along the longitudinal axis is received in the recess of the bonding pad to meet at least one of the spaced apart portions of the surrounding side wall and wherein a second portion of the terminal lead side wall extending along the longitudinal axis and opposite at least that part of the first portion meeting with the one of the spaced apart portions of the surrounding side wall is exposed and not in contact with the bonding pad;

c) securing the terminal lead to the bonding pad at least at a region where the one of the first and second contact walls having the recess meets the second portion of the terminal lead; and d) directly contacting the other of the first and second contact walls not having the recess to an enclosure for the implantable medical device.

* * * * *